United States Patent

Neu

Patent Number: 5,714,758
Date of Patent: Feb. 3, 1998

[54] PORTABLE INFRARED SURFACE INSPECTION SYSTEM

[75] Inventor: John T. Neu, Solana Beach, Calif.

[73] Assignee: Surface Optics Corp., San Diego, Calif.

[21] Appl. No.: 731,156

[22] Filed: Oct. 10, 1996

[51] Int. Cl.$^6$ ............................................. G01J 5/02
[52] U.S. Cl. ........................ 250/339.08; 250/339.11; 250/341.8
[58] Field of Search ...................... 250/339.08, 339.11, 250/339.12, 341.8

[56] References Cited

U.S. PATENT DOCUMENTS 5,118,945  6/1992  Winschuh et al. ............... 250/358.1

Primary Examiner—Don Wong
Attorney, Agent, or Firm—Gregory Garmong

[57] ABSTRACT

A compact, portable infrared surface inspection system includes an infrared point energy source having an infrared energy source, an aperture plate having an aperture therethrough, and a pair of 90-degree off-axis parabolic mirrors that focus infrared energy from the infrared energy source to the aperture. A third 90-degree off-axis parabolic mirror receives the infrared energy passing through the aperture, which is located at the focus of the third 90-degree off-axis parabolic mirror, and reflects the infrared energy through a 90-degree angle into a Fourier transform infrared spectrometer having as a infrared energy output an FHR beam. The FFIR beam is optionally filtered and directed into a final mirror array that includes a barrel ellipse mirror assembly which receives the FTIR beam, directs the FTIR beam toward a specimen analysis location at a first focus of the ellipse, and directs a diffuse scattered beam from the specimen analysis location toward a second focus of the ellipse. An infrared detector is located at the second focus of the ellipse. A single housing encloses these elements. The housing has a specimen port at the specimen analysis location, whereby a specimen to be analyzed may be placed at the specimen analysis location.

17 Claims, 5 Drawing Sheets

PORTABLE INFRARED SURFACE INSPECTION SYSTEM

BACKGROUND OF THE INVENTION

This invention relates to an infrared spectrometer, and, more particularly, to a portable spectrometer apparatus useful for inspecting surfaces for foreign substances such as contamination.

The chemical cleanliness of surfaces is an important influence on the operability of many processing and manufacturing operations on articles. It is necessary to determine the mount and type of any foreign substances that may be present at the surface of an article, and whether attempts to remove the foreign substances have been successful. In a commonly encountered example, surface contamination in the form of grease or other organic substances on the surface of an article may prevent its being adhesively bonded to another article, because the adhesive cannot adhere to the grease-coated surface. The grease may initially be present either intentionally as a protective layer or unintentionally due to contamination. There may have been prior attempts to remove the grease from the surface, as with solvent-cleaning procedures. In these cases, it is desirable to determine whether the surface to be bonded is truly free of the contaminant prior to the attempt to perform adhesive bonding. Partial cleaning may lead to partial bonding, a situation that can be worse than no bonding at all, because the partial bonding state may go undetected and there may be an erroneous belief that full bonding has been achieved.

There are many other instances where it is necessary to determine the presence of small amounts of chemicals at a surface. For example, small amounts of residues of explosives on surfaces may lead to an understanding of the nature and cause of a disaster such as an aircraft crash. Pesticide residues are often concentrated at the surfaces of plant foods. Surface chemistries of plastics and other materials may change over time. The continuity and composition of surface coatings must be determined.

A number of technologies are known for detecting and measuring contaminants at surfaces. In one, infrared spectroscopy of infrared energy reflected from a surface is used to chemically characterize the surface. As an example, U.S. Pat. No. 5,088,821 describes an infrared spectroscopic analysis system. Although this and similar types of systems have proved useful in analyzing bulk materials and surfaces in laboratory environments, they have drawbacks. An important concern is that such systems are large in size, require extensive set-up, alignment, and calibration prior to use, and lack the robustness required for use in a field or factory environment.

There is, accordingly, a need for an infrared surface analysis system that is useful at sites and in applications where conventional infrared spectrometers cannot be used. The present invention fulfills this need, and further provides related advantages.

SUMMARY OF THE INVENTION

The present invention provides a system, apparatus, and method for analyzing surfaces to determine their cleanliness or chemical contamination. The approach permits infrared quantitative and qualitative analysis of a wide variety of convex, flat, concave, and rough surfaces. The surface analysis apparatus is a complete, integrated unit. It is relatively compact and light, so that it is readily handled and operated by one person. The apparatus is rugged and may be sealed against intrusion of dirt, gases, and chemicals that adversely affect its performance.

In accordance with the invention, a compact, portable infrared surface inspection apparatus comprises an infrared point energy source, which itself comprises an infrared energy source, and optionally an aperture plate having an aperture therethrough and a pair of 90-degree off-axis parabolic mirrors to focus and size the infrared output of the infrared energy source. In the preferred approach, the pair of mirrors includes a first 90-degree off-axis parabolic mirror that receives infrared energy from the infrared energy source and reflects the infrared energy from the infrared energy source through 90 degrees. The infrared energy source is located at a focus of the first 90-degree off-axis parabolic mirror, so that the reflected beam is a parallel beam. The pair of mirrors further includes a second 90-degree off-axis parabolic mirror that receives infrared energy reflected from the first 90-degree off-axis parabolic mirror and reflects the infrared energy from the first 90-degree off-axis parabolic mirror through 90 degrees to a focus of the second 90-degree off-axis parabolic mirror. Where present, the aperture of the apemire plate is located at the focus of the second 90-degree off-axis parabolic mirror.

The apparatus includes a third 90-degree off-axis parabolic mirror that receives the infrared energy from the second 90-degree off-axis parabolic mirror and reflects the infrared energy through a 90-degree angle. The focus of the second 90-degree off-axis parabolic mirror and the focus of the third 90-degree off-axis parabolic mirror are coincident. A Fourier transform infrared spectrometer has as an input the infrared energy reflected from the third 90-degree off-axis parabolic mirror and as an output an FTIR beam. Optionally, the FTIR beam is passed titrough a band pass filter.

A final mirror array includes a barrel ellipse mirror assembly which receives the FTIR beam, directs the FTIR beam toward a specimen analysis location at a first focus of the ellipse, and directs a diffuse scattered beam from the specimen analysis location toward a second focus of the ellipse. An infrared detector is located at the second focus of the ellipse and detects the scattered beam. There is a single housing, which preferably is purged by a gas flow, within which the infrared point energy source, the third 90-degree off-axis parabolic mirror, the Fourier transform infrared spectrometer, the band pass filter, and the final mirror array are contained. The housing has a specimen port (which may have a window therein) at the specimen analysis location, whereby a specimen to be analyzed may be placed at the specimen analysis location.

Two types of final mirror arrays have been developed. Both types employ a cylinder with an internal ellipsoidal reflective mirror surface (termed the barrel ellipse mirror) having its major axis coincident with the cylinder center axis, and a fourth 90-degree off-axis parabolic mirror located in the center of the barrel ellipse mirror and positioned to focus the FTIR beam to the specimen port at normal incidence thereto and coaxial with the ellipse major axis.

In the first type, the barrel ellipse mirror has a beam opening therethrough to admit the FTIR beam perpendicular to the major axis of the ellipse (or, alternatively stated, coincident with the minor axis of the ellipse). An optional flat mirror laterally external to the barrel ellipse mirror is positioned to direct the FTIR beam through the beam opening in the barrel ellipse mirror. The fourth 90-degree off-axis parabolic mirror located at the center of the barrel ellipse mirror is positioned to focus the FTIR beam to the specimen.

In the second type of final mirror array, the barrel ellipse mirror has a beam opening at a first end thereof laterally adjacent to the second focus of the barrel ellipse. The beam opening receives the FTIR beam therethrough, parallel to the major axis of the ellipse. A flat mirror is positioned to direct the FTIR beam along the minor axis of the ellipse. The fourth 90-degree off-axis parabolic mirror located at the center of the barrel ellipse mirror is positioned to focus the FTIR beam to the specimen port at normal incidence thereto and coaxial with the ellipse major axis. In this embodiment, the FTIR beam is introduced into the end of the barrel ellipse, parallel to the ellipse major axis but laterally displaced by a small amount therefrom. By introducing the FTIR beam into the barrel ellipse parallel to and close to the major axis of the ellipse, the cross sectional area of the final mirror array may be made smaller than possible with the first type of final mirror array. The final mirror array may therefore be used inside small recesses, most effectively having concave surfaces, which otherwise would be inaccessible for infrared spectroscopic measurements.

A working embodiment of this measurement apparatus built by the inventor has dimensions of 9¾ inches high, 8¼ inches wide, and 11 inches deep. This fully integrated and unitized apparatus weighs less than about 20 pounds, and in the preferred embodiment weighed 18 pounds. Support equipment in the form of a computer to control the measurements, and store and process data, a purge-gas source, and a power source is required. However, the support equipment may be connected to the measurement apparatus by an umbilical cable that may be up to 100 or more feet in length, allowing the measurement apparatus to be readily moved about and operated by one person while the heavier and more bulky support equipment remains stationary. This system has produced excellent results in measuring surface chemical properties in a variety of simulated working environments.

There are many requirements in industry to make infrared reflectance-transmittance measurements of opaque concave surfaces in confined areas, as for example inside of pipes, hemispheres, and closed containers. The present approach provides a geometry that allows such measurements inside confined spaces. This capability to measure inside recesses is enhanced by a change in the shape of the base of the barrel ellipse mirror assembly so as, in part, to conform approximately to a hemispherical surface, as will be discussed subsequently in relation to FIG. 3 as compared with FIG. 2.

The system of the present invention is particularly useful because of its portability and robustness in a non-laboratory environment. Existing infrared spectrometer systems of this general type are large, bulky, and heavy, and also require careful set-up prior to performing measurements. Their use is largely limited to the laboratory environment, which is clean and where the measurement apparatus is not subject to the physical wear-and-tear of a non-laboratory environment. The present measurement apparatus is relatively small, light in weight, robust, and easily handled by one person. The housing around all of the optical elements of the measurement apparatus protects those elements from physical damage and contamination, and prevents their misalignment in day-to-day usage. The measurement apparatus is readily moved to remote locations away from a laboratory setting, and then used to perform infrared spectrometric measurements without extensive prior set-up. After one measurement is performed, the measurement apparatus is easily moved to another location for another measurement.

The present invention thus provides an important advance in the art of infrared spectrometers. Optimization of the optical train allows the instrument to be light in weight, small in size, and operable by one person. It is sufficiently ragged to be used at sites remote from a conventional laboratory environment, such as a factory floor or a field site of an investigation. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
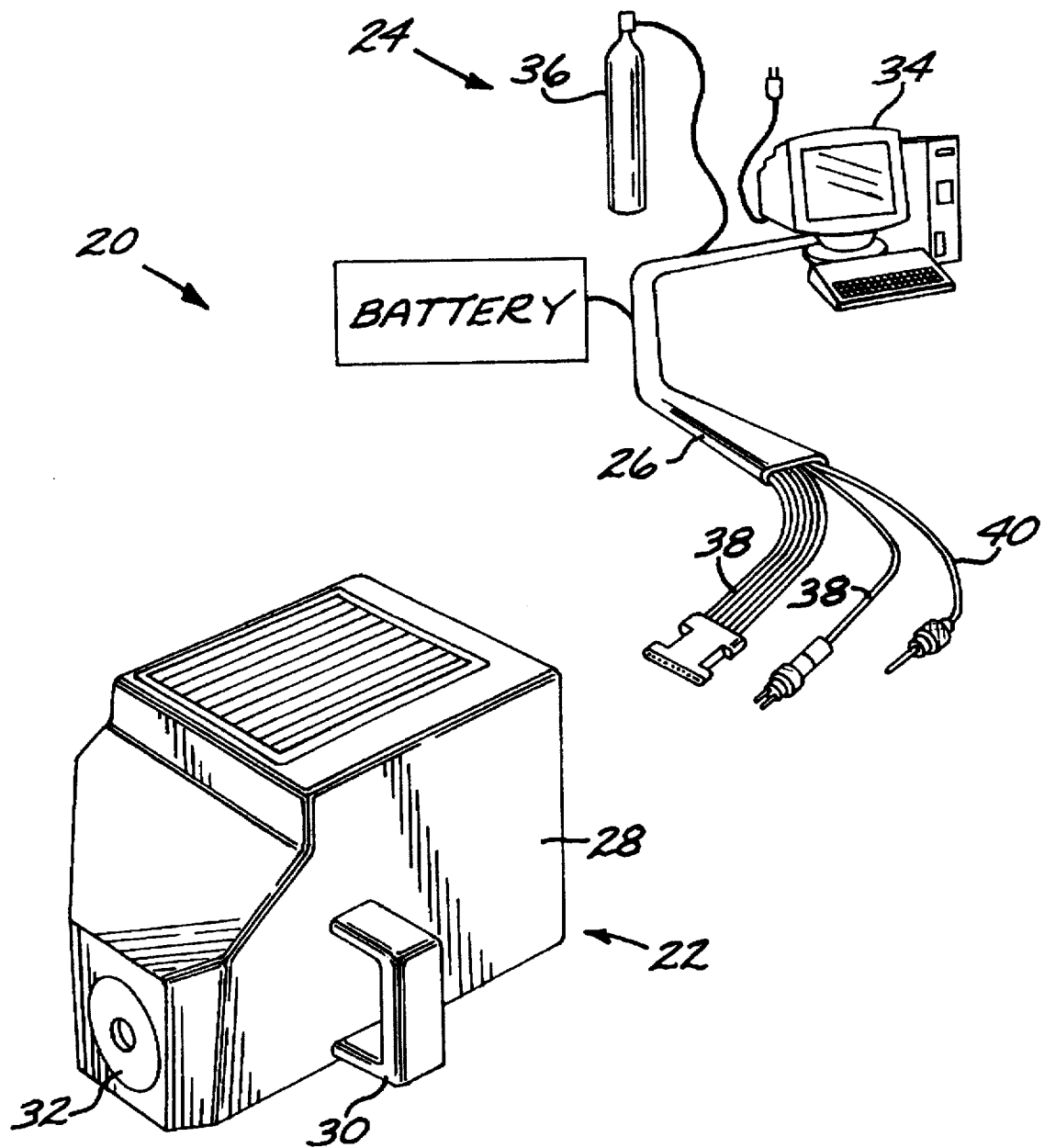
FIG. 1 is a schematic perspective view of a measurement system for performing infrared surface inspections.

FIG. 1 depicts a system 20 used to inspect surfaces of solids. The system 20 includes a measurement apparatus 22 and support equipment 24, connected by an umbilical cable 26. The support equipment 24 may be relatively stationary, as by being built into a base or supported on a rolling cart. The measurement apparatus 22 is easily moved about by hand or mounted to a mechanical measurement support (not shown). The support equipment 24 may also be carried with the measurement apparatus 22, as in a backpack worn by the operator of the system, and connected to the measurement apparatus 22 by a relatively short umbilical cable 26, resulting in complete portability of the entire system.

The measurement apparatus 22 is a compact, portable unit with all operating components contained within one housing 28 having handles 30 thereon for ease of grasping and manipulating by an operator. A specimen port 32 in the housing 28 is placed against a surface to be measured. The support equipment 24 includes a computer 34 that controls the measurement apparatus 22, receives data therefrom, stores the data, analyzes the data, and reports the data. The interior of the measurement apparatus 22 may optionally be purged with an inert gas to avoid spurious readings due to carbon dioxide and water vapor in the air which would otherwise fill the measurement apparatus. Where the measurement apparatus is to be purged, a purge gas source 36 is also provided in the support equipment 24.

The umbilical cable 26 extends between the support equipment 24 and the measurement apparatus 22. The umbilical cable 26 includes electrical instrumentation, electrical grounding, and power lines 38 and a gas flow line 40 for conducting the purge gas from the source 36 to the measurement apparatus 22. The umbilical cable 26 may be disconnected at one end from the measurement apparatus 22 or the support equipment 24, as needed, and then reconnected for operation of the system. The umbilical cable 26 may be as long as necessary for the intended applications, but is typically on the order of 100 feet or less. In one form, the support equipment is relatively stationary and the measurement apparatus 22 is carried by hand or by a support mechanism (such as a robotic arm) to various locations within the reach of the umbilical cable. In the backpack form, the support equipment is carried on the back of the operator and connected to the measurement apparatus by a relatively short umbilical cable.

In the illustrated embodiment, the power provided to the measurement apparatus 22 is 110 volt AC power. The power may instead be DC power, as from a battery located in the support equipment or in the measurement apparatus 22 itself. The battery-powered version is particularly useful in a fully portable embodiment wherein the support equipment 24 is carried in a backpack or the like. Various arrangements utilizing the elements depicted in FIG. 1 may be employed. For example, although FIG. 1 illustrates the computer 34 as remote from the measurement apparatus 22 and connected thereto by the umbilical cable, the computer may equivalently be built into the measurement apparatus 22 as a dedicated-purpose microcomputer responsive to a trigger command from the operator of the system.

Figure 2:
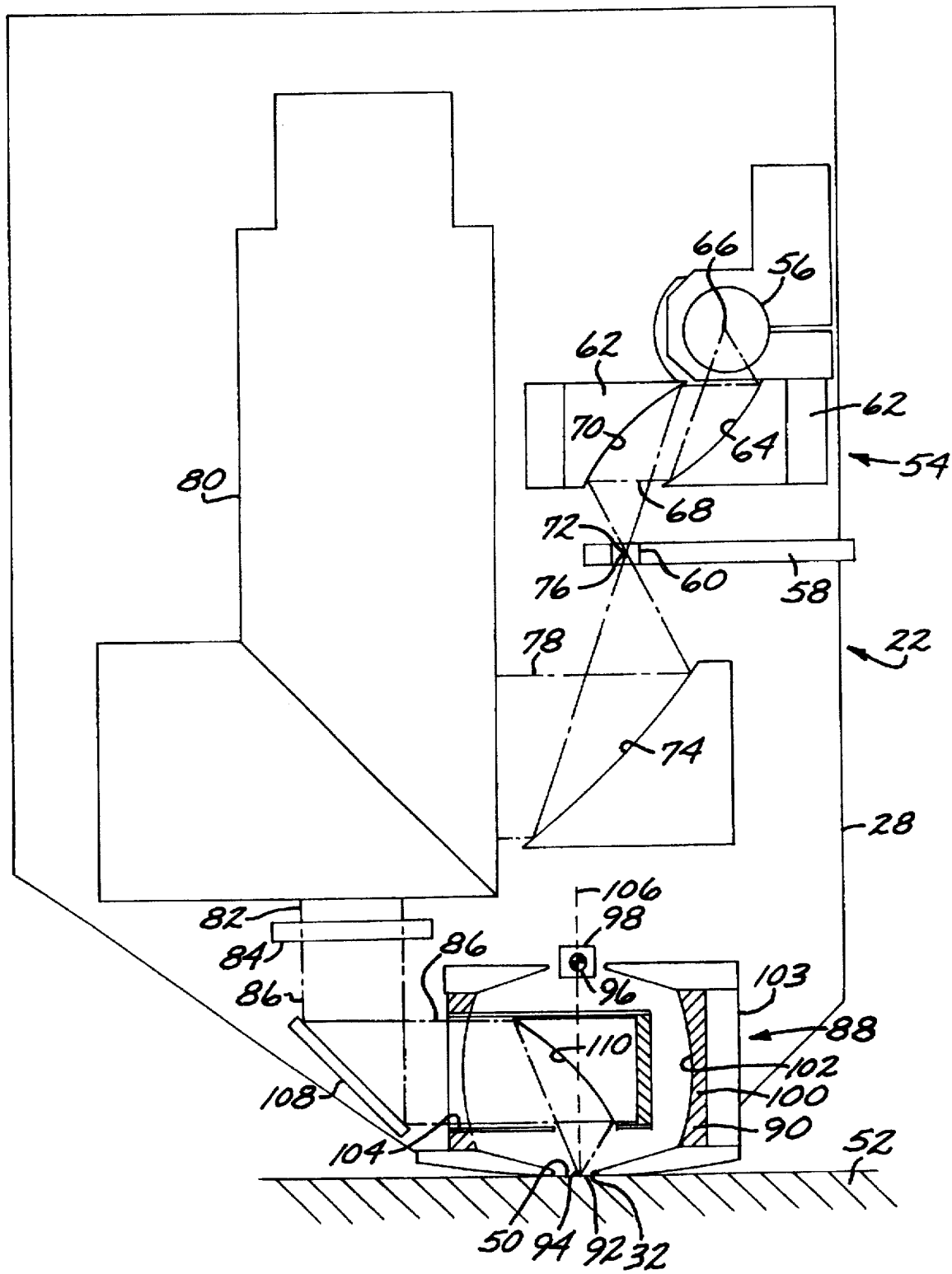
FIG. 2 is a schematic side sectional view of a first embodiment of the apparatus according to the invention, using a first type of final mirror array.
Figure 3:
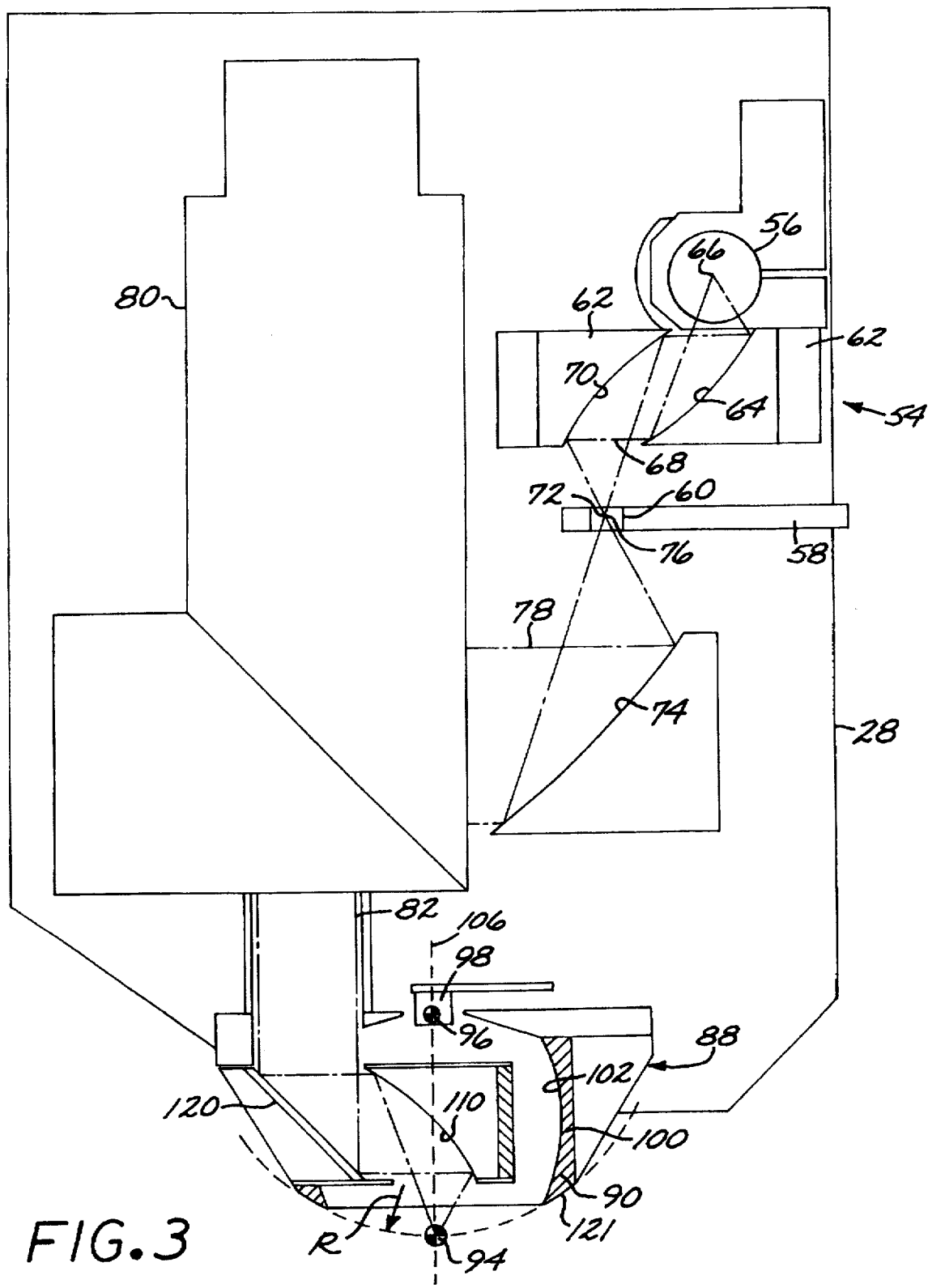
FIG. 3 is a schematic side sectional view of a second embodiment of the apparatus according to the invention, using a second type of final mirror array.

FIGS. 2 and 3 depict two embodiments of the measurement apparatus 22 in greater detail. Referring to FIG. 2, the measurement apparatus 22 is used to measure a surface 50 of a solid body 52, by placing the specimen port 32 of the housing 28 into contact, or closely adjacent to, the surface 50.

The housing 28 includes a broadband infrared point energy source 54. The infrared point energy source 54 is in the 2-25 micrometer wavelength range in a preferred version, but it may be provided in other ranges as well. In the preferred embodiment, the infrared point energy source 54 has an infrared energy source 56, such as a resistively heated element, an optional aperture plate 58 with an aperture 60 therethrough, and an optional pair of mirrors 62 directing the infrared energy from the energy source 56 through the aperture 60. The use of the aperture 60 and pair of mirror 62 is preferred to provide a precisely defined point source of infrared energy, whose lateral extent (beam diameter) is also well controlled, in a compact space. Other operable beam defining and shaping optics may be used.

The pair of mirrors 62 preferably includes a first 90-degree off-axis parabolic ("OAP") mirror 64, selected and positioned so that the infrared energy source 56 is at its focus 66. The first OAP mirror 64 receives the infrared energy from the infrared energy source 56 and reflects that infrared energy as a parallel beam 68 through an angle of 90 degrees. The parallel beam 68 is incident along the parallel axis of a second 90-degree OAP mirror 70, which reflects the beam 68 through 90 degrees and to the aperture 60, which lies at a focus 72 of the second 90-degree OAP mirror 70. The aperture 60 is not required, because the beam 68 is reflected to the focus 72 of the second 90-degree OAP mirror 70, but it is desirably present because the infrared energy source 56 has a finite lateral dimension. The infrared energy passing through the focus 72 and the optional aperture 60 serves as a fine point source of infrared energy. The infrared point energy source 54 thus provides a highly compact infrared point energy source.

The infrared energy passing through the focus 72 and the optional aperture 60 is reflected through an angle of 90 degrees by a third 90-degree OAP mirror 74. The aperture 60 is located at a focus 76 of the third 90-degree OAP mirror 74. (That is, the focus 72 of the second 90-degree OAP mirror 70 and the focus 76 of the third 90-degree OAP mirror 74 are coincident.) The reflected beam is therefore an infrared parallel beam 78.

A Fourier transform infrared spectrometer 80 receives the beam 78 at an entry thereto. The Fourier transform infrared spectrometer 80 is a known device utilizing a beam splitter, a fixed mirror, and a moving minor. Such devices are available commercially, as for example from MIDAC Corp or Nicolet Analytical Instruments. An infrared parallel unfiltered FTIR beam 82 exits the spectrometer 80. The parallel FTIR beam 82 is optionally passed through a band-pass filter 84 so as to select a specific frequency of the infrared energy, producing a parallel beam termed the filtered FTIR beam 86. In the following description, the filtered FTIR beam 86 is discussed, although the unfiltered FTIR beam 82 may instead be used.

The filtered FTIR beam 86 is provided to a final mirror array 88. The final mirror array 88 includes a barrel ellipse mirror assembly 90 that receives the filtered FTIR beam 86 and directs the filtered FTIR beam toward a specimen analysis location 92 at a first focus 94 of the barrel ellipse mirror assembly 90. The specimen port 32, which in operation is pressed against or held adjacent to the surface 50 (the latter if scratching of the surface is a concern), is located at the specimen analysis location 92. The barrel ellipse minor assembly 90 directs a diffusely scattered beam from the surface 50 at the specimen analysis location 92 toward a second focus 96 of the barrel ellipse mirror assembly 90. An infrared detector 98 is located at the second focus 96. If there is any specular reflection of the incident infrared beam from the surface 50, it is blocked by the barrel ellipse mirror assembly and does not reach the infrared detector 98.

FIG. 2 illustrates one preferred configuration of the final mirror array 88, and FIG. 3 illustrates a second preferred configuration.

Referring further to FIG. 2, the final mirror array 88 includes a barrel ellipse mirror 100 having an elliptical reflective mirror surface 102 within a generally cylindrical housing 103, a beam opening 104 through the elliptical mirror surface 102, and an ellipse major axis 106 coincident with the cylindrical axis of the housing 103. A flat mirror 108 exterior to the barrel ellipse mirror 100 directs the filtered FTIR beam 86 through the beam opening 104 at an angle perpendicular to the ellipse major axis 106 (i.e., coincident with an ellipse minor axis). A fourth 90-degree OAP mirror 110 is located within the internal cavity of the barrel ellipse mirror 100 along the ellipse major axis 106 at a location midway between the first focus 94 and the second focus 96. The fourth 90-degree OAP mirror 110 is oriented to reflect the parallel filtered FTIR parallel beam 86 that passes through the beam opening 104 through an angle of 90 degrees so as to be concentric with the ellipse major axis 106 and converge at the first focus 94 of the barrel ellipse mirror 100. When a surface 50 is present at the fast focus 94, infrared energy is diffusely scattered from that surface 50 and is reflected to the detector 98 at the second focus 96, as previously described.

FIG. 3 illustrates another preferred configuration. In the embodiment of FIG. 3, elements common with the configuration of FIG. 2 are assigned the same reference numbers, and their discussion is incorporated here. For the purpose of illustration, no filter 84 is used in this embodiment, and the beam entering the final mirror array is the unfiltered FTIR beam 82. In this embodiment, the barrel ellipse mirror 100 is slotted to receive a flat mirror 120 that is located partly external to, and partly internally within, the cavity of the barrel ellipse mirror 100. The FTIR beam 82 enters the barrel ellipse mirror 100 through its end, parallel to the ellipse axis major 106. The FTIR beam 82 is reflected through 90 degrees by the flat mirror 120, to a direction perpendicular to the ellipse major axis 106. The FTIR beam 82 reflects from the fourth OAP mirror 110 to converge at the first focus 94, and thereafter the optical path is the same as that described in relation to the embodiment of FIG. 2.

The configuration of FIG. 3 has important advantages in some applications. In the configuration of FIG. 2, wherein the FTIR beam enters the side of the barrel ellipse perpendicular to its major axis, the final mirror array 88 has a relatively wide transverse dimension. In the configuration of FIG. 3, wherein the FTIR beam enters the end of the barrel ellipse parallel to its major axis and closely spaced thereto, the final mirror array 88 is much narrower and smaller in cross section as compared with the embodiment of FIG. 2. Also, as illustrated, the lower end of the barrel ellipse may be shortened and shaped, as indicated at numeral 121, so that the entire final mirror array 88 fits within a spherical form having a preselected radius R. Consequently, the final mirror array 88 may be placed into narrow cavities of diameter 2R whose bottom surfaces are to be chemically analyzed.

Using variations and modifications within the scope of the approach discussed in relation to FIGS. 1–3, a variety of surface analysis systems useful in specific situations may be prepared. An elongated tubular extension may be added to the apparatus 22 to position the final mirror array 88 at an arbitrarily deep location within the cavity, and the geometry of the final mirror array 88 may be selected to perform measurements on the bottom or sides of the cavity. The tubular extension is preferably made of brass with an reflective internal gold coating. This form of tubular extension is a structural element that is robust and suitable for use in locations outside the laboratory. This structural tube is distinct from a tube made of glass or other relatively brittle material whose use is confined to the laboratory.

Figure 4:
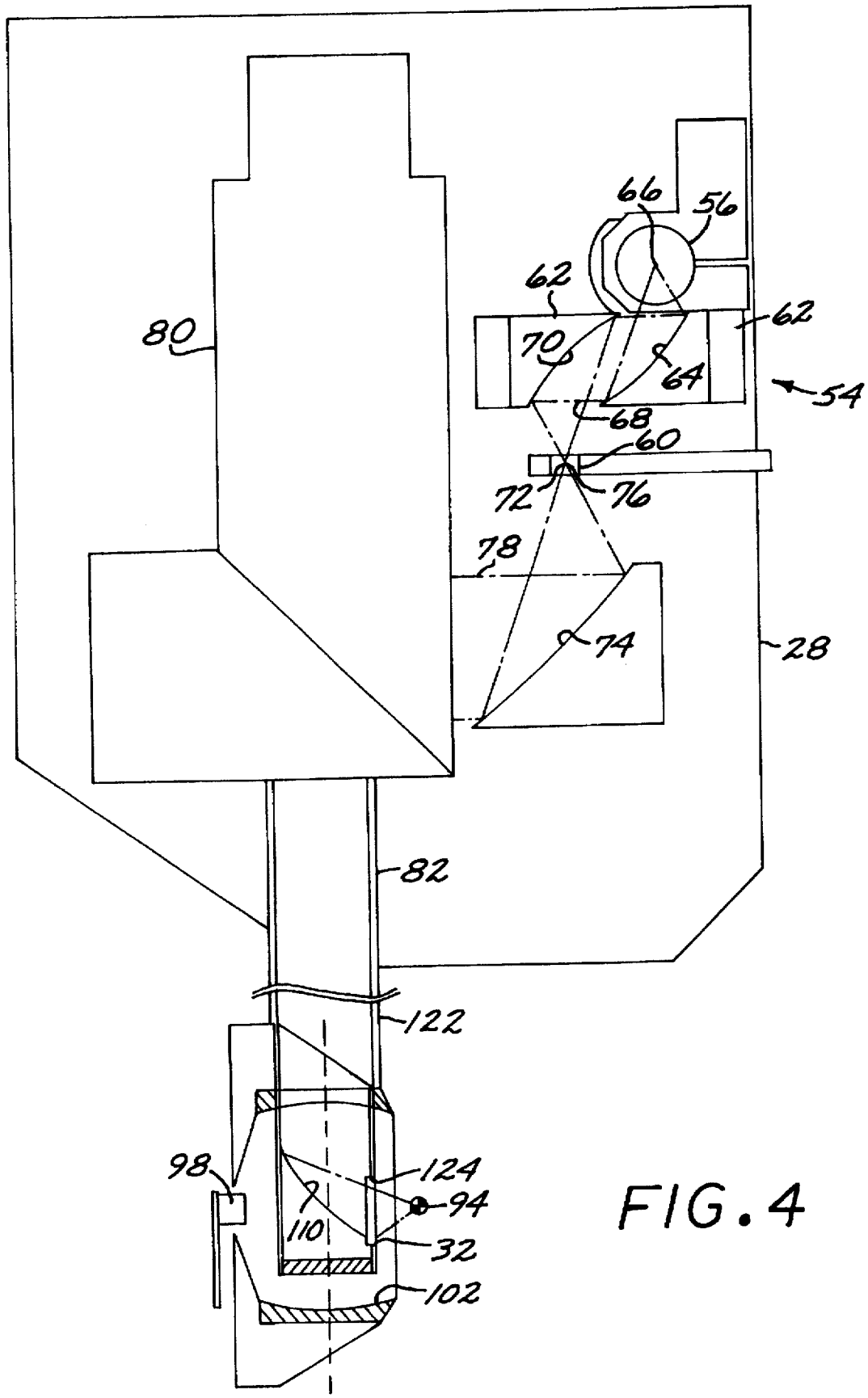
FIG. 4 is a schematic side sectional view of a third embodiment of the apparatus according to the invention, using a tubular extension.

In the embodiment of FIG. 4, elements common with the configurations of FIGS. 2 and 3 are assigned the same reference numbers, and their discussion is incorporated here. FIG. 4 illustrates an embodiment wherein a tubular extension 122 positions the final mirror array 88 at a location spaced below the housing 28, and wherein the final mirror array 88 introduces the FTIR beam through the side of the barrel ellipse mirror 100 without any flat mirror. The specimen port 32 is in the side of the tubular extension 122. This geometry allows the sides of an arbitrarily deep cavity to be analyzed. The geometry of the final mirror array 88 as shown in FIG. 3 may also be used with the tubular extension 122, to perform measurements at the bottoms of cavities of diameter 2R or more and of arbitrary depth. Also as shown in FIG. 4, but applicable to all embodiments, an infrared-transparent window 124 made of a material such as potassium bromide (KBr) may be provided at the specimen port 32 to prevent contaminants from reaching the mirrors and other components inside the apparatus 22.

A system 20 according to FIGS. 1 and 2 of the invention has been constructed and operated by the inventor. In this system 20, the computer 34 included a 133 MHz Pentium™ processor with MIDAC/GRAM 386 software, the purge gas source 36 was a bottom of compressed nitrogen with a pressure and flow regulator, and the umbilical cable 26 was 10 feet long. The housing 28 was 9¾ inches high, 8¼ inches wide, and 11 inches deep, and the apparatus 22 weighed 18 pounds. Within the apparatus 22, the infrared energy source 56 was a resistive heater whose temperature was determined by the current flowing therethrough. The 90-degree OAP mirrors 64, 70, and 110 with effective focal lengths of 1 inch were purchased commercially from Aero Research Associates, Port Washington, N.Y. The 90-degree OAP mirror 74 with an effective focal length of 2 inches was purchased commercially from MIDAC Corp., Irvine, Calif. The aperture 60 was used, and had a diameter of 2 millimeters. The Fourier transform infrared spectrometer was purchased commercially from MIDAC Corp., Irvine, Calif. The bandpass filter 84 was used, and was purchased from OCLI, Santa Rosa, Calif. The barrel ellipse mirror 100 was a 3.010 inch long aluminum cylinder, diamond-turned on the inside to form an ellipse of revolution with the ellipse major axis coincident with the cylinder center axis. The foci 94 and 96 were 2 inches apart. The cylindrical portion of the barrel ellipse mirror 100 was shortened as indicated at numeral 121 of FIG. 3 at a location slightly inside the focus 94. The detector 98 was a DLATGS unit operating at ambient (room) temperature.

Figure 5:
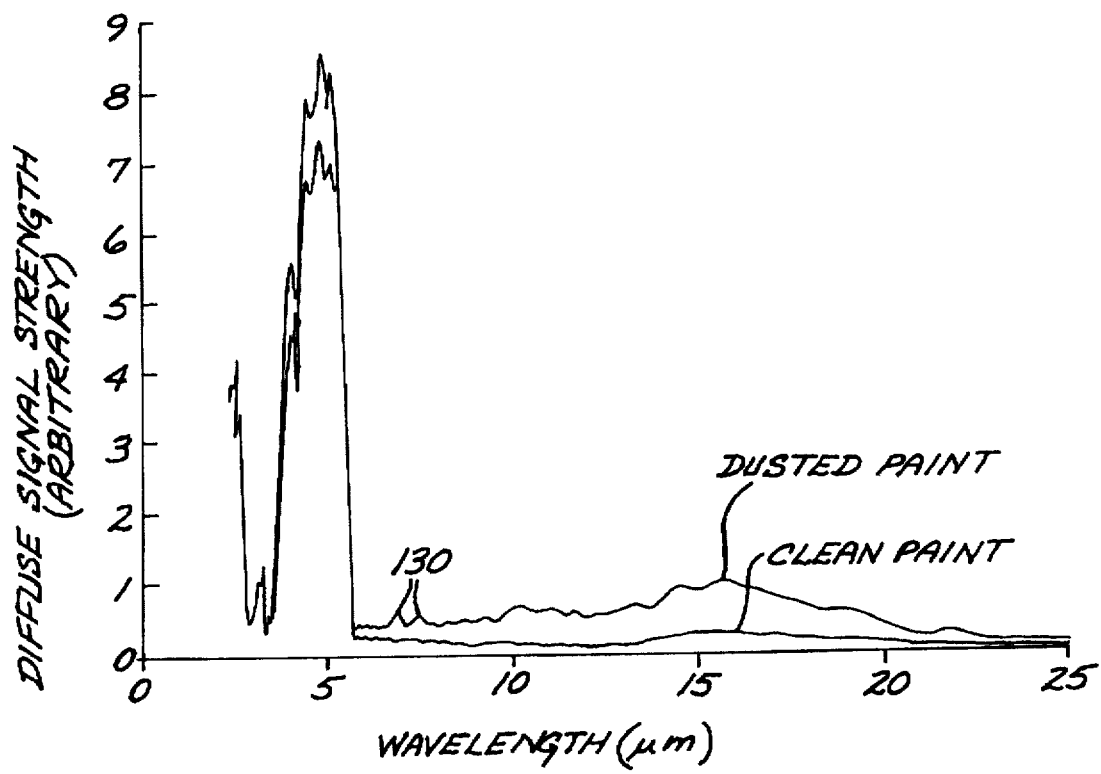
FIG. 5 is a graph of signal strengths as a function of wavelength measured using the working embodiment of the invention.
Figure 6:
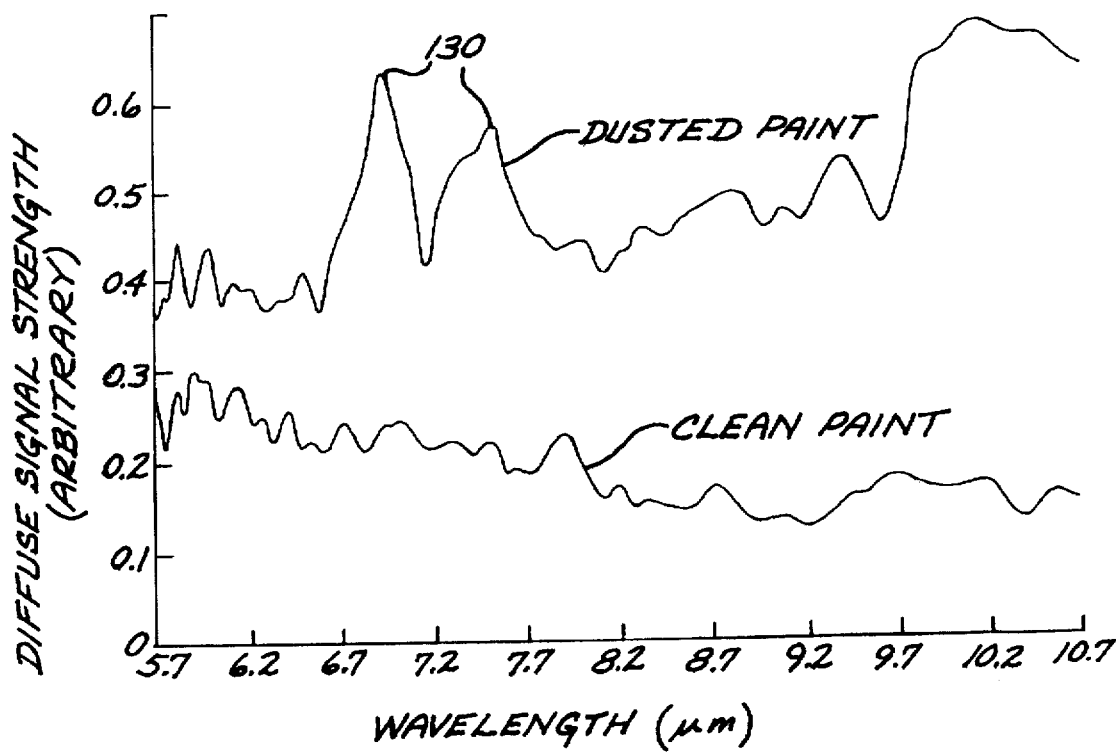
FIG. 6 is a detail of the graph of FIG. 5.

FIG. 5 illustrates spectra of signal strength as a function of wavelength obtained using the system 20, and FIG. 6 is a detail of a portion of the spectra. A piece of painted automobile sheet material was first measured, and its spectrum is indicated as "Clean Paint". The same piece was thereafter dusted with an ammonium nitrate powder, and the excess powder was removed. The spectrum for this article is indicated as "Dusted Paint". Peaks in the spectrum for the Dusted Paint indicated at numeral 130 correspond to the presence of residual ammonium nitrate on the surface of the article.

The present invention provides an important advance in the art of infrared spectroscopy. The measurement apparatus is integrated, compact, portable, and may be carried and operated by one person. The entire system may be made portable using a backpack approach for the support equipment. There is no set-up and alignment of optical components required. The measurement apparatus may be used to make a series of measurements of large fixed objects at different positions and angles, and inside cavities and recesses. The embodiment wherein the FTIR beam enters the final mirror assembly parallel to the major axis of the barrel ellipse is particularly well suited for making measurements inside small cavities and recesses.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A compact, portable infrared surface inspection system, the system including a measurement apparatus comprising:
   an infrared point energy source comprising
      an infrared energy source having an infrared energy output, and
      a pair of 90-degree off-axis parabolic mirrors, the pair of mirrors comprising
         a first 90-degree off-axis parabolic mirror that receives infrared energy from the infrared energy source and reflects the infrared energy from the infrared energy source through 90 degrees, the infrared energy source being located at a focus of the first 90-degree off-axis parabolic mirror, and
         a second 90-degree off-axis parabolic mirror that receives infrared energy reflected from the first 90-degree off-axis parabolic mirror and reflects the infrared energy from the first 90-degree off-axis parabolic mirror through 90 degrees to a focus of the second 90-degree off-axis parabolic mirror;

a third 90-degree off-axis parabolic mirror that receives the infrared energy from the second 90-degree off-axis parabolic mirror and reflects the infrared energy through a 90-degree angle, the focus of the second 90-degree off-axis parabolic mirror being coincident with the focus of the third 90-degree off-axis parabolic mirror;

a Fourier transform infrared spectrometer having as a infrared energy input the infrared energy reflected from the third 90-degree off-axis parabolic mirror and as a infrared energy output an FTIR beam;

a final mirror array having as an input the FTIR beam, the final mirror assembly comprising a barrel ellipse mirror assembly which receives the FTIR beam, directs the FTIR beam toward a specimen analysis location at a first focus of the ellipse, and directs a scattered beam from the specimen analysis location toward a second focus of the ellipse;

an infrared detector located at the second focus of the ellipse; and a single housing within which the infrared point energy source, the third 90-degree off-axis parabolic mirror, the Fourier transform infrared spectrometer, and the final mirror array are contained, the housing having a specimen port at the specimen analysis location, whereby a specimen to be analyzed may be placed at the specimen analysis location.

2. The system of claim 1, wherein an apertutus further includes an aperture plate having an aperture therethrough, the aperture being located at the focus of the second 90-degree off-axis parabolic mirror.

3. The system of claim 1, wherein the apparatus further includes a band pass filter disposed between the Fourier transform infrared spectrometer and the final mirror array, such that the FTIR beam passes therethrough.

4. The system of claim 1, wherein the final mirror array comprises a barrel ellipse mirror having an internal elliptical reflective mirror surface, a beam opening therethrough, and an ellipse axis, a flat mirror external to the barrel ellipse mirror and positioned to direct the FTIR beam through the beam opening in the barrel ellipse mirror, a fourth 90-degree off-axis parabolic mirror located at the center of the barrel ellipse mirror, the fourth 90-degree off-axis parabolic mirror being positioned to focus the FTIR beam to the specimen port at normal incidence thereto and coaxial with the ellipse axis.

5. The system of claim 1, wherein the final mirror array comprises a barrel ellipse mirror having an internal elliptical reflective mirror surface, a beam opening at a first end thereof adjacent to the second focus of the barrel ellipse, and an ellipse axis, the beam opening being positioned to receive the FTIR beam therethrough parallel to the ellipse axis, a flat mirror positioned to direct the FTIR beam in a direction perpendicular to the ellipse axis, a fourth 90-degree off-axis parabolic mirror located at the center of the barrel ellipse mirror, the fourth 90-degree off-axis parabolic mirror being positioned to focus the FTIR beam received from the flat mirror to the specimen port at normal incidence thereto and coaxial with the ellipse axis.

6. The system of claim 1, wherein the apparatus further includes a tubular extension extending from the housing and having an extension axis, wherein the final mirror array is supported on the tubular extension.

7. The system of claim 6, wherein the final mirror array comprises a barrel ellipse mirror having an internal elliptical reflective mirror surface, a beam opening therethrough, and an ellipse major axis lying perpendicular to the extension axis, and a fourth 90-degree off-axis parabolic mirror located at the center of the barrel ellipse mirror, the fourth 90-degree off-axis parabolic mirror being positioned to focus the FTIR beam entering through the beam opening to the specimen port at normal incidence thereto and coaxial with the ellipse axis.

8. The system of claim 1, wherein the apparatus further includes an infrared-transparent window covering the specimen port.

9. The system of claim 1, wherein the system further includes a battery in electrical communication with the infrared energy source.

10. The system of claim 1, wherein the system further includes support equipment, and an umbilical cable extending from the support equipment to the measurement apparatus.

11. The system of claim 10, wherein the support equipment includes a computer receiving as an input an output signal of the detector.

12. The system of claim 10, wherein the support equipment includes a battery in electrical communication with the infrared energy source.

13. The system of claim 10, wherein the support equipment includes a source of a purge gas, and wherein the umbilical cable includes a gas-flow line in communication with the interior of the measurement apparatus.

14. A compact, portable infrared surface inspection system, the system including a measurement apparatus comprising:

an infrared point energy source;

a 90-degree off-axis parabolic mirror that receives the infrared energy from the infrared point energy source and reflects the infrared energy through a 90-degree angle, the focus of the 90-degree off-axis parabolic mirror being coincident with the infrared point energy source;

a Fourier transform infrared spectrometer having as a infrared energy input the infrared energy reflected from the 90-degree off-axis parabolic mirror and as a infrared energy output an FTIR beam;

a final mirror array having as an input the FTIR beam, the final mirror assembly comprising a barrel ellipse mirror assembly which receives the FTIR beam, directs the FTIR beam toward a specimen analysis location at a first focus of the ellipse, and directs a scattered beam from the specimen analysis location toward a second focus of the ellipse;

an infrared detector located at the second focus of the ellipse; and a single housing within which the infrared point energy source, the 90-degree off-axis parabolic mirror, the Fourier transform infrared spectrometer, and the final mirror array are contained, the housing having a specimen port at the specimen analysis location, whereby a specimen to be analyzed may be placed at the specimen analysis location.

15. A method of making infrared measurements, comprising the steps of:

providing a measurement apparatus comprising
an infrared point energy source,
a 90-degree off-axis parabolic mirror that receives the infrared energy from the infrared point energy source and reflects the infrared energy through a 90-degree angle, the focus of the 90-degree off-axis parabolic mirror being coincident with the infrared point energy source,
a Fourier transform infrared spectrometer having as a infrared energy input the infrared energy reflected from the 90-degree off-axis parabolic mirror and as a infrared energy output an FTIR beam,
a final mirror array having as an input the FTIR beam, the final mirror assembly comprising a barrel ellipse mirror assembly which receives the FTIR beam, directs the FTIR beam toward a specimen analysis location at a first focus of the ellipse, and directs a scattered beam from the specimen analysis location toward a second focus of the ellipse,
an infrared detector located at the second focus of the ellipse, and
a single housing within which the infrared point energy source, the 90-degree off-axis parabolic mirror, the Fourier transform infrared spectrometer, and the final mirror array are contained, the housing having a specimen port at the specimen analysis location, whereby a specimen to be analyzed may be placed at the specimen analysis location;

transporting the measurement apparatus to a site remote from a laboratory setting; and performing infrared spectroscopy measurements at the site using the measurement apparatus.

16. The method of claim 15, wherein the step of performing includes the step of a person holding the measurement apparatus as the infrared spectroscope measurements are performed.

17. The method of claim 15, wherein the step of providing a measurement apparatus includes the step of providing a measurement apparatus having a weight of less than about 20 pounds.

* * * * *